United States Patent [19]

Boudakian

[11] Patent Number: 4,521,603

[45] Date of Patent: Jun. 4, 1985

[54] CONTINUOUS PROCESS FOR THE PRODUCTION OF POLYBROMOPYRIDINE COMPOUNDS

[75] Inventor: Max M. Boudakian, Pittsford, N.Y.

[73] Assignee: Olin Corporation, Cheshire, Conn.

[21] Appl. No.: 462,845

[22] Filed: Feb. 1, 1983

[51] Int. Cl.$^3$ .................. C07D 213/61; C07D 213/72; C07D 213/80; C07D 211/84

[52] U.S. Cl. .................................... 546/304; 546/345; 546/318; 546/307; 546/321

[58] Field of Search ............... 546/345, 318, 304, 307, 546/321

[56] References Cited

U.S. PATENT DOCUMENTS 1,977,662 10/1934 Wibaut et al. ....................... 546/345
3,849,422 11/1974 Weis .................................... 546/345
3,974,166 8/1976 Mutterer ............................. 546/345

OTHER PUBLICATIONS

H. J. den Hertog, Jr. et al., Rec. Trav. Chim., 51, 381–388, 940–950, 1932.
S. M. McElvain et al., J. Amer. Chem. Soc., 65, 2227–2233 (1943).
W. H. Levelt et al., Rec. Trav. Chim. 49, 466–473, 1930.

*Primary Examiner*—Henry R. Jiles
*Assistant Examiner*—Robert C. Whittenbaugh
*Attorney, Agent, or Firm*—James B. Haglind; Donald F. Clements

[57] ABSTRACT

A continuous process for producing a polybromopyridine compound comprises admixing a polychloropyridine compound with an anhydrous water soluble solvent in a first reaction zone to form a solution of the polychloropyridine compound. Hydrogen bromide gas is introduced into the solution while maintaining the temperature in the range of from about 70° to about 140° C. to produce a solution of the polybromopyridine compound. The solution is cooled to a temperature in the range of from about 5° to about 35° C. to precipitate the polybromopyridine compound from the anhydrous solvent. The polybromopyridine compound is separated from the anhydrous solvent and the anhydrous solvent is returned to the first reaction zone. Polybromopyridine compounds of increased purity are produced in a process having reduced material, energy and operating costs. The process does not require the use of water or other co-solvents nor the distillation of the reaction product mixture.

9 Claims, 3 Drawing Figures

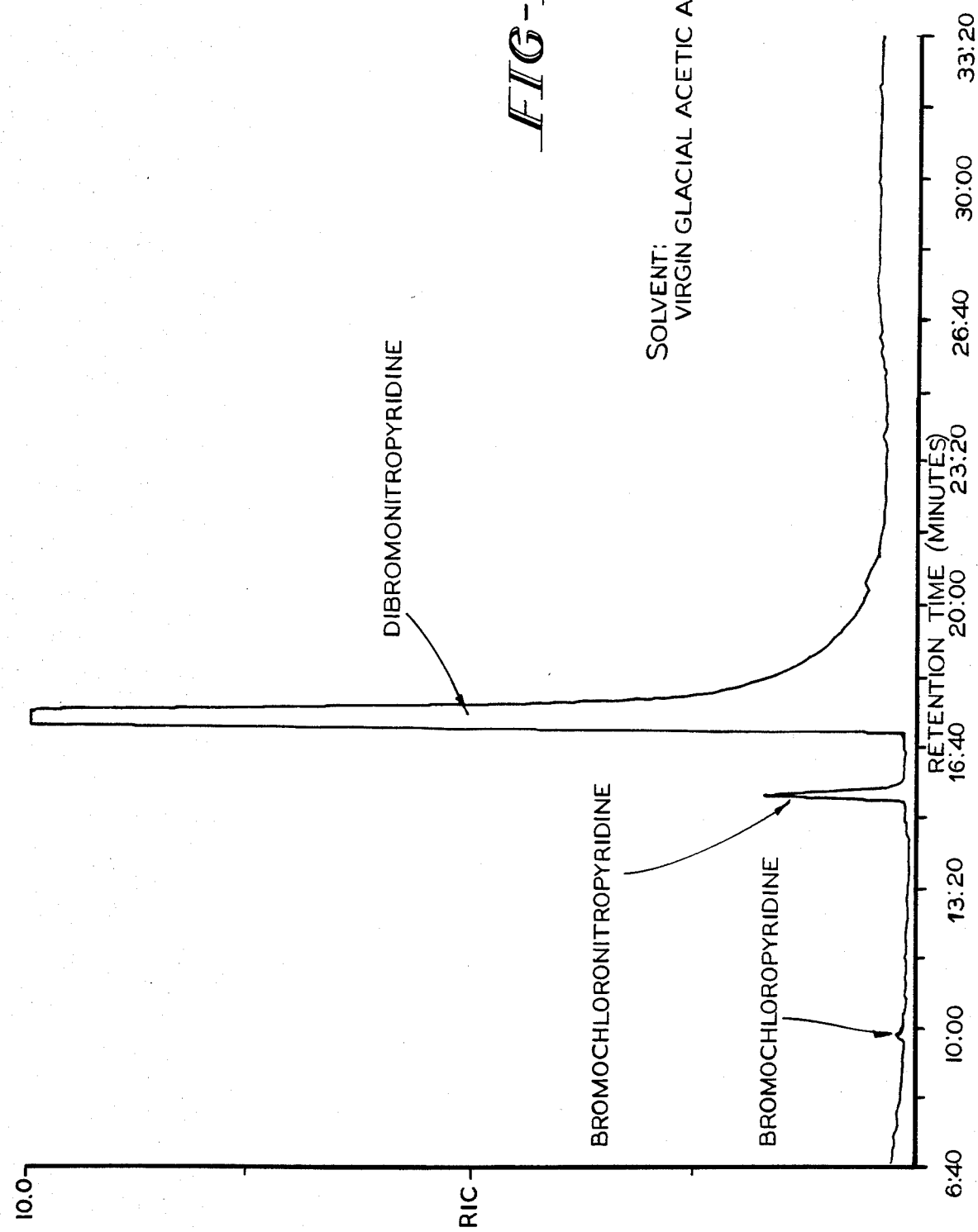

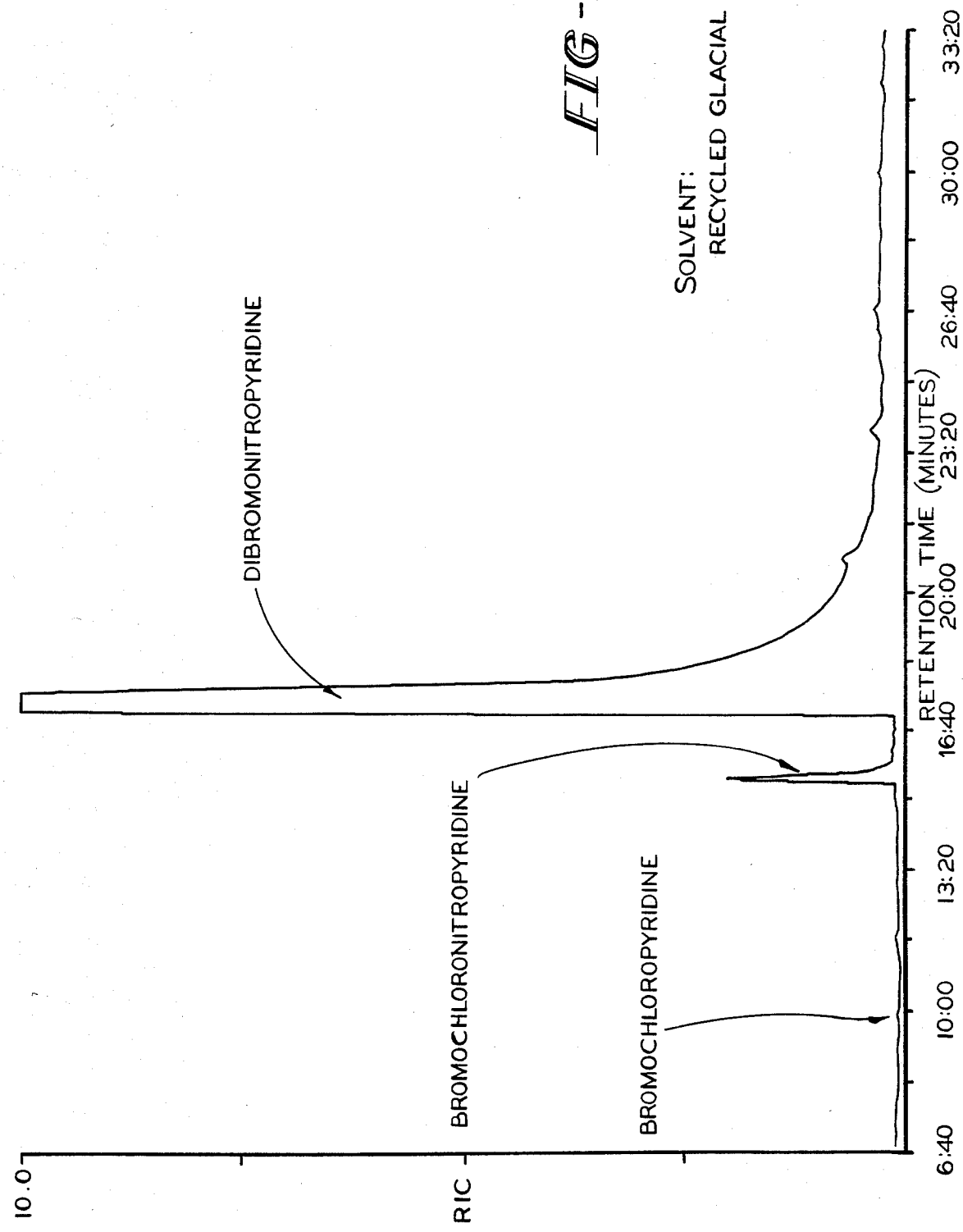

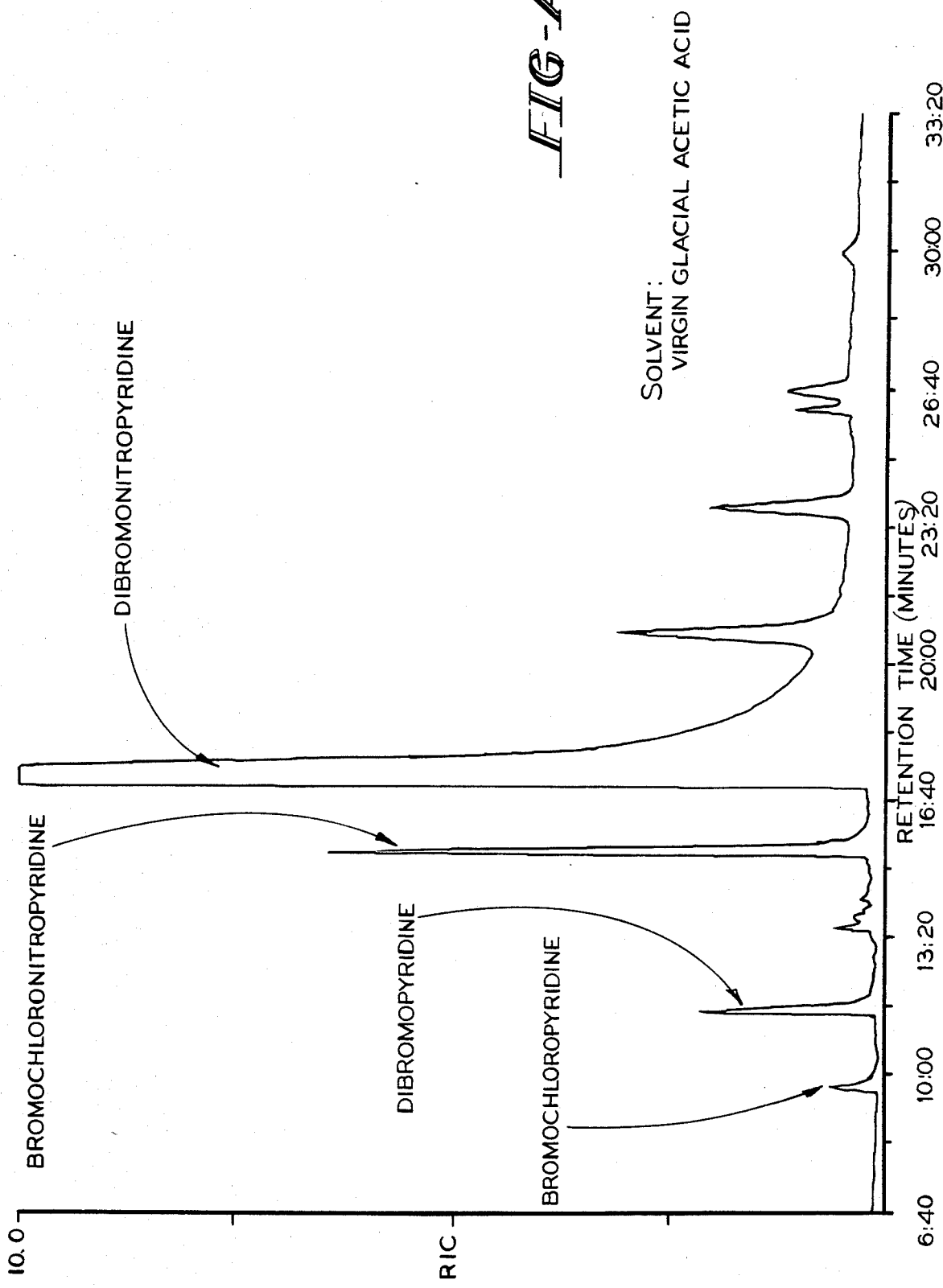

CONTINUOUS PROCESS FOR THE PRODUCTION OF POLYBROMOPYRIDINE COMPOUNDS

The present invention is directed to a process for producing polybromopyridine compounds. Polybromopyridine compounds are used to control or destroy fungi which attack fruits and field crops.

Polybromopyridine compounds having the bromine atoms directly attached to the pyridine ring such as dibromopyridine or tribromopyridine have been prepared by the bromination of pyridine or monobromopyridine. For example, H. J. den Hertog, Jr. and J. P. Wibaut (Rec. Trav Chim. 51, 381–388, 940–950 (1932); U.S. Pat. No. 1,977,662, issued Oct. 23, 1934) conducted vapor phase brominations of 2-bromopyridine at temperatures in the range of 300° to 500° C. in the presence of pumice and metal bromides. The product reaction mixture was made basic with an alkali metal carbonate and steam distilled to form 2,5- and 2,6-dibromopyridine, 2,3,5- and 2,3,6-tribromopyridine and 2,3,5,6-tetrabromopyridine. This reaction results in the formation of a polymeric product which is the major reaction product and, in addition, takes place at a reaction rate so low that it is impractical for commercial purposes.

2,6-Dibromopyridine is recovered from the reaction product of pyridine vapor with bromine vapor in a special reaction column at 500° C. as described by S. M. McElvain and M. A. Goese (J. Amer. Chem. Soc. 65, 2227–2233, 1943). The reaction mixture was washed with a caustic soda solution and steam distilled; the distillation was separated into an oil and aqueous phase and the aqueous phase extracted with benzene. After combining the benzene extraction and the oil phase, fractional distillation gave 2,6-dibromopyridine in 17% yield.

The reaction of 4-carboxy-2,6-dihydroxypyridine (citrazinic acid) with phosphorous oxybromide at 170° C. gave a reaction product which was steam distilled and the distillation residue filtered while hot. The crystals recovered were recrystallized several times in hot water to give 4-carboxy-2,6-dibromopyridine in 25% yield, as reported by W. H. Levelt and J. P. Wibaut [Rec. Trav. Chim. 49, 466–473, 1930].

Polybromopyridine compounds have also been prepared by the reaction of phosphorous oxybromide with 3-bromo-3-bromomethyl glutarimide at temperatures in the range of 95° to 120° C. The reaction mixture is cooled to 20° C. and then quenched in ice water. The precipitate recovered is dissolved in diethyl ether, extracted with water, and dried over magnesium sulfate. The ether is removed in a rotary evaporator, the crude product dissolved in boiling cyclohexane, and the solution cooled to 15°–20° C. to give 2,6-dibromo-3-bromomethyl pyridine (U.S. Pat. No. 3,849,422, issued Nov. 19, 1974, to C. Weis).

F. Mutterer describes the preparation of polybromopyridine compounds by the reaction of polychloropyridine compounds with gaseous hydrogen bromide in an anhydrous organic solvent at temperatures between 80° and 130° C. in U.S. Pat. No. 3,974,166, issued Aug. 10, 1976. To isolate the reaction products, the reaction mixture is poured onto ice or into ice water or the solvent is removed by vaporizing the solvent and HBr in vacuo and recrystallizing the product from water.

In all of the above processes, the recovery of the polybromopyridine compounds requires a multi-step operation which is both costly and time consuming. Where a solvent or reaction medium is used, the solvent is either highly diluted with water, making it uneconomic to recover or evaporated in methods which are energy intensive and thus costly.

There is a need therefore for a continuous process for the production of polybromopyridine compounds in which products of high purity can be recovered efficiently and at reduced cost. Additionally, there is a need for an energy efficient continuous process for the production of polybromopyridine compounds.

It is an object of the present invention to provide a continuous process for the production of polybromopyridine compounds.

Another object of the present invention is to provide a continuous process for the production of polybromopyridine compounds having increased purity.

An additional object of the present invention is to provide a continuous process for the production of polybromopyridine compounds having improved solvent recovery.

These and other objects of the invention are accomplished in a continuous process for producing a polybromopyridine compound which comprises:

(a) admixing a polychloropyridine compound with an anhydrous water soluble solvent in a first reaction zone to form a solution of the polychloropyridine compound;

(b) introducing hydrogen bromide gas into the solution of the polychloropyridine compound while maintaining the solution at a temperature in the range of from about 80° to about 140° C. to produce a solution of the corresponding polybromopyridine compound;

(c) cooling the solution to a temperature in the range of from about 5° to about 35° C. to precipitate the polybromopyridine compound from the anhydrous water soluble solvent;

(d) separating the polybromopyridine compound from the anhydrous water soluble solvent in a separation zone; and (e) returning the anhydrous water soluble solvent to the first reaction zone.

FIG. 1 is a mass spectrograph of 2,6-dibromo-3-nitropyridine produced by the process of the present invention in which the solvent was virgin glacial acetic acid.

FIG. 2 is a mass spectrograph of a 2,6-dibromo-3-nitropyridine produced by the process of the present invention in which the solvent was recycled glacial acetic acid.

FIG. A is a mass spectrograph of 2,6-dibromo-3-nitropyridine produced by a process of the prior art in which the solvent was virgin glacial acetic acid.

In the novel process of the present invention, polychloropyridine compounds are employed as one reactant. Suitable polychloropyridine compounds are 2,6-dichloropyridine and derivatives thereof represented by the structural formula:

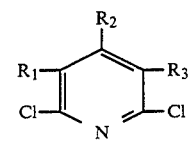

I where $R_1$ and $R_3$ independently represent hydrogen, a halogen atom or an amino, nitro, halomethyl or carboxylic acid group; $R_2$ represents hydrogen, a halogen atom, or an alkyl, haloalkyl or carboxylic acid group; the alkyl group being methyl, ethyl, propyl or isopropyl.

Typical polychloropyridine compounds include:
2,6-Dichloropyridine
4-Bromo-2,6-dichloropyridine
2,6-Dichloro-3-nitropyridine
2,6-Dichloro-3-aminopyridine
2,6-Dichloro-3-chloromethylpyridine
2,6-Dichloro-3-bromomethylpyridine
2,6-Dichloro-4-trichloromethylpyridine
2,6-Dichloro-3-trifluoromethylpyridine
2,6-Dichloro-3-chloromethyl-5-nitropyridine
2,6-Dichloronicotinic Acid
2,6-Dichloroisonicotinic Acid
2,3,6-Trichloropyridine
2,4,6-Trichloropyridine
2,5,6-Trichloro-3-nitropyridine
2,3,6-Trichloro-5-aminopyridine
2,5,6-Trichloro-3-aminopyridine
2,5,6-Trichloro-3-chloromethylpyridine
2,5,6-Trichloronicotinic Acid
2,3,6-Trichloro-4-ethylpyridine
2,3,4,6-Tetrachloropyridine
2,3,5,6-Tetrachloropyridine
4-Bromo-2,3,5,6-tetrachloropyridine.

Produced by the process of the reaction as polybromopyridine compounds are 2,6-dibromopyridine and derivatives represented by the structural formula

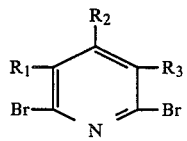

II where $R_1$, $R_2$ and $R_3$ are as defined above.

Typical polybromopyridine compounds produced in the novel process of the present invention include:
2,6-Dibromopyridine
2,4,6-Tribromopyridine
2,6-Dibromo-3-nitropyridine
2,6-Dibromo-3-aminopyridine
2,6-Dibromo-3-chloromethylpyridine
2,6-Dibromo-3-bromomethylpyridine
2,6-Dibromo-4-trichloromethylpyridine
2,6-Dibromo-3-trifluoromethylpyridine
2,6-Dibromo-3-chloromethyl-5-nitropyridine
2,6-Dibromonicotinic acid
2,6-Dibromoisonicotinic acid
2,6-Dibromo-3-chloropyridine
2,6-Dibromo-4-chloropyridine
2,6-Dibromo-5-chloro-3-nitropyridine
2,6-Dibromo-3-chloro-5-aminopyridine
2,6-Dibromo-5-chloro-3-aminopyridine
2,6-Dibromo-5-chloro-3-chloromethylpyridine
2,6-Dibromo-5-chloronicotinic acid
2,6-Dibromo-3-chloro-4-ethylpyridine
2,6-Dibromo-3,4-dichloropyridine
2,6-Dibromo-3,5-dichloropyridine
2,4,6-Tribromo-3,5-dichloropyridine.

Preferred polybromopyridine compounds produced by the process of the present invention include those of formula II above in which $R_1$, $R_2$ and $R_3$ are independently selected from the group consisting of hydrogen, a halogen atom, an amino, nitro or halomethyl group. Examples of the preferred polybromopyridine compounds include:
2,6-dibromopyridine
2,6-dibromo-3-nitropyridine
2,6-dibromo-3-aminopyridine
2,6-dibromo-3-chloropyridine
2,6-dibromo-3,5-dichloropyridine
2,6-dibromo-3-bromomethyl-5-nitropyridine
2,6-dibromo-3-nitro-5-chloropyridine To produce polybromopyridine compounds using the process of the present invention, the polychloropyridine substrate is dissolved in an anhydrous water soluble organic solvent including glacial acetic acid, and lower aliphatic alcohols having from 1 to about 4 carbon atoms such as ethanol, propanol, isopropanol, and butanol, with glacial acetic acid being the preferred solvent. The solution of the polychloropyridine compound has a mole ratio of polychloropyridine compound to solvent of from about 1:10 to about 1:50, and preferably from about 1:15 to about 1:40.

Gaseous hydrogen bromide is reacted with the polychloropyridine substrate in solution in a first reaction zone to displace chlorine atoms attached directly to the pyridine ring, and form the corresponding polybromopyridine compound.

Sufficient amounts of hydrogen bromide are used to assure high yields of the polybromopyridine compounds and to remove the hydrogen chloride produced. Mole ratios of HBr to the polychloropyridine substrate are preferably in the range of from about 6:1 to about 10:1. While the reaction is normally conducted at atmospheric pressure, reduced amounts of hydrogen bromide may be employed if the reaction is conducted under pressure, for example, at pressures in the range of from about 10 to about 125 atmospheres.

During the reaction of the gaseous hydrogen bromide with the polychloropyridine substrate, the solution temperature is maintained at a temperature in the range of from about 70° to about 140° C., and preferably at from about 80° to about 120° C.

Reaction times are controlled to minimize the formation of unwanted by-products such as monobromopyridine compounds. Suitable reaction times are those in the range of from about 1 to about 12 and preferably from about 2 to about 8 hours.

Following the reaction period, the solution of polybromopyridine compound is cooled to a temperature in the range of from about 5° to about 35° C., and preferably from about 10° to about 30° C., to precipitate the polybromopyridine compound.

The crystalline polybromopyridine compound formed on cooling the solution is separated from the anhydrous solvent by any suitable solid-liquid separation method such as, for example, filtering or centrifuging.

The anhydrous solvent recovered during the separation is substantially free of hydrogen halides and can be directly recycled to the first reaction zone without further treatment.

After separation from the anhydrous solvent, the crystalline polybromopyridine compound is washed with water to remove any occluded solvent and then dried.

The gaseous mixture of hydrogen bromide containing hydrogen chloride recovered from the first reaction zone can be treated in one of several ways including separating the gases by condensing the mixture at low temperatures or feeding the gaseous mixture to a scrubber containing, for example, sodium hydroxide to produce a mixture of NaBr and NaCl. The bromine values may be recovered by treating the mixture with chlorine gas.

Employing the novel process of the present invention results in the production of polybromopyridine compounds of high purity. In contrast to methods of the prior art, separation and recovery of the polybromopyridine compound takes place in the absence of water or other co-solvents, resulting in the recovery of the anhydrous solvent which can be directly recycled to the process. In addition, distillation of the reaction product mixture is unnecessary. This recovery method significantly reduces material, energy and operating costs.

The following examples and comparisons are given to further illustrate the process of the present invention. All percentages and proportions are by weight unless otherwise indicated.

EXAMPLE 1

Gaseous HBr (3.0 moles; 245 g.) was introduced to a pre-heated mixture (110° C.) of 2,6-dichloropyridine (0.5 mole; 74.2 g.) in glacial acetic acid (1050 g.; 17.5 moles) over a 7 hour period to produce a reaction mixture having a mole ratio of HBr to 2,6-dichloropyridine of 6:1. An aliquot (52.4 g.) was removed and cooled to 15°–25° C. The crystalline slurry was filtered and the mother liquor recovered. Water-washing of the filter cake to remove occluded acetic acid followed by air-drying gave a product having a m.p. of 113° C. and identified by VPC assay as 2,6-dibromopyridine 93.8%; 2-bromo-6-chloropyridine, 5.5%.

COMPARATIVE EXAMPLE A

An aliquot (52.02 g.) of the hot reaction mixture produced in EXAMPLE 1 was quenched with 345 ml. $H_2O$ at 0° C. The reaction slurry was filtered, water-washed and air-dried to give a product (m.p. 113° C.) identified by VPC assay as 2,6-dibromopyridine 91.1%; 2-bromo-6-chloropyridine 8.9%.

EXAMPLE 2

To the reaction mixture of EXAMPLE 1 additional HBr (0.5 mole; 40 g.) was introduced over a one hour period to increase the mole ratio of HBr to 2,6-dichloropyridine to 7 to 1. An aliquot (wt. 51.13 g.) was cooled to 15°–25° C. to produce a crystalline slurry. The slurry was filtered and the mother liquor recovered. The filter cake was washed with water and air dried to give a product (m.p. 119° C.) having a VPC assay as 2,6dibromopyridine, 98.8%; 2-bromo-6-chloropyridine 1.1%.

COMPARATIVE EXAMPLE B

An aliquot (50.93 g.) of the reaction mixture produced in EXAMPLE 2 was quenched with 577 ml $H_2O$ (0° C.), the slurry formed was filtered and air dried to give a product (m.p. 115°–116° C.) having a VPC assay as 2,6-dibromopyridine, 94.7%; 2-bromo-6-chloropyridine, 5.3%.

EXAMPLE 3

Gaseous hydrogen bromide (3.5 moles; 283 g.) was added to a solution of 2,6-dichloropyridine (0.5 mole; 74.2 g.) in glacial acetic acid (1050 g.; 17.5 moles) heated to 110° C. over an 8 hour period. The reaction mixture was cooled to 25° C. and 2,6-dibromopyridine was filtered. (The filtrate, wt. 1051 g., was transferred to the reactor as recycle solvent for the next bromination).

Filtered 2,6-dibromopyridine was washed with water to remove occluded acetic acid and air dried to give 53.4 g. (0.23 mole) of water-white product, m.p. 119.6° C. VPC: 98.8% 2,6-dibromopyridine; 1.1% 2-bromo-6-chloropyridine.

EXAMPLE 4

To the filtrate from EXAMPLE 3 (wt. 1051 g.) was charged 2,6-dichloropyridine (0.5 mole; 74.5 g.). Anhydrous hydrogen bromide (3.5 moles; 282 g.) was introduced over a 7 hour period to the heated (110° C.) solution.

The bromination mixture was cooled to 25° C. and 2,6-dibromopyridine filtered. Again the filtrate, wt. 929 g., was transferred to the bromination reactor for recycle operations.

Filtered 2,6-dibromopyridine was washed with water to remove occluded acetic acid and air dried to give 0.51 mole (120 g.) of water-white product, m.p. 118.5°–119.5° C. VPC Assay, 95.7% 2,6-dibromopyridine; 4.1% 2-bromo-6-chloropyridine.

In EXAMPLES 1–4 and COMPARATIVE EXAMPLES A and B, VPC assay was carried out in a stainless steel column (6'×0.25") packed with 10% Carbowax 20M coated on Chromasorb W (60/80 mesh). The retention times (in minutes) were 2,6-dichloropyridine, 5.4; 2-bromo-6-chloropyridine, 8.1; and 2,6-dibromopyridine, 12.6.

EXAMPLE 5

Gasesous HBr (0.94 mole; 76 g.) was passed into a pre-heated (80° C.) solution of 2,6-dichloro-3-nitropyridine (0.1 mole; 19.3 g.) in glacial acetic acid (105 g.; 1.75 moles) over a 2-hour period. The reaction mixture was cooled to 10° C. and filtered to separate 2,6-dibromo-3-nitropyridine. (The filtrate, wt. 107 g., was recovered and returned to the reactor as recycle solvent).

Filtered 2,6-dibromo-3-nitropyridine was washed with water to remove any occluded acetic acid and dried in a vacuum oven (50° C.), wt. 12.4 g. (0.044 mole) of product, m.p. 86°–87° C. HPLC assay (area %): 99.8%. (HPLC column: ZORRAX O.D.S. Mobile phase, 60% $CH_3CN/H_2O$. Column Temperature: 50° C.).

EXAMPLE 6

To the mother liquor from EXAMPLE 5 (107 g.) was charged, 2,6-dichloro-3-nitropyridine (13.2 g.; 0.0684 mole). Anhydrous hydrogen bromide (55 g.; 0.68 mole) was introduced over a 2.5 hour period to the heated (80° C.) solution. The reaction mixture was cooled to 10° C. and 2,6-dibromo-3-nitropyridine filtered. (The filtrate, wt. 93.5 g., was set aside for recycle operations). The filter cake was washed with water to remove any occluded acetic acid and dried in a vacuum oven (40°–50° C.), wt. 23.3 g. (0.083 mole) of product, m.p. 86°–87° C. HPLC assay (area %): 100%.

COMPARATIVE EXAMPLE C

Gaseous HBr (0.74 mole; 60 g.) was introduced to a pre-heated mixture (80° C.) of 2,6-dichloro-3-nitropyridine (0.1 mole; 19.3 g.) in glacial acetic acid (3.5 moles; 210 g.) over a 4-hour period. The hot bromination liquor was transferred to 1 liter of water (0° C.), 2,6- dibromo-3-nitropyridine filtered, water-washed and dried in a vacuum oven (50° C.) to constant weight (22.4 g., 0.0795 mole; m.p. 85°-86° C. (1,2): m.p. 78° C.). (HPLC assay (area %): 99.4%).

Mass spectra data for EXAMPLES 5 and 6 and COMPARATIVE EXAMPLE C are illustrated in FIGS. 1, 2 and FIG. A, respectively. The analyses were made on a Finnegan 4023 Mass Spectrograph having an Incos Data System utilizing a six foot glass 3% SP 2250 column programmed from 60-275 at 8/min. with He gas flow at 25 cc/min. As illustrated in FIGS. 1 and 2, the novel process of the present invention on produced 2,6-dibromo-3-nitropyridine having only minute amounts bromochloropyridine and bromochloronitropyridine as impurities even when recycled solvent was employed. FIG. A, using the process of the prior art described in U.S. Pat. No. 3,974,166, issued Aug. 10, 1976, to F. Mutterer (Example No. 7, columns 5 and 6), produces 2,6-dichloro-3-nitropyridine, however, having significant amounts of bromochloronitropyridine and dibromopyridine as well as other impurities which are not formed using the process of the present invention.

What is claimed is:

1. A continuous process for producing a polybromopyridine compound which comprises:
   a. admixing a polychloropyridine compound with an anhydrous water soluble solvent selected from the group consisting of glacial acetic acid and lower aliphatic alcohols having from 1 to about 4 carbon atoms in a first reaction zone to form a solution of the polychloropyridine compound;
   b. introducing hydrogen bromide gas into the solution of polychloropyridine compound while maintaining the solution at a temperature in the range of from about 70° to about 140° C. to produce a solution of the corresponding polybromopyridine compound;
   c. cooling the solution to a temperature in the range of from about 5° to about 35° C. to precipitate the polybromopyridine compound from the anhydrous water soluble solvent;
   d. separating the polybromopyridine compound from the anhydrous water soluble solvent in a separation zone; and
   e. returning the anhydrous water soluble solvent to the first reaction zone.

2. The process of claim 1 in which the polychloropyridine compound is represented by the formula:

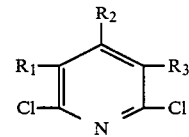

where $R_1$ and $R_3$ independently represent hydrogen, a halogen atom or an amino, nitro, halomethyl or carboxylic acid group; $R_2$ represents hydrogen, a halogen atom, or an alkyl, haloalkyl or carboxylic acid group; the alkyl group being methyl, ethyl, propyl or isopropyl.

3. The process of claim 2 in which the solution of polychloropyridine compound has a mole ratio of polychloropyridine compound to anhydrous water soluble solvent of from about 1:10 to about 1:50.

4. The process of claim 3 in which the mole ratio of hydrogen bromide to polychloropyridine compound is from about 6:1 to about 10:1.

5. The process of claim 4 in which $R_1$, $R_2$ and $R_3$ are independently selected from the group consisting of hydrogen, a halogen atom, or an amino, nitro, or halomethyl group.

6. The process of claim 5 in which the anhydrous water soluble solvent is glacial acetic acid.

7. The process of claim 6 in which the polybromopyridine compound is 2,6-dibromopyridine.

8. The process of claim 6 in which the polybromopyridine compound is cooled to a temperature in the range of from about 10° to about 15° C.

9. The process of claim 8 in which the polybromopyridine compound is 2,6-dibromo-3-nitropyridine.

* * * * *